(12) United States Patent
Matsushita

(10) Patent No.: US 10,527,501 B2
(45) Date of Patent: Jan. 7, 2020

(54) RESISTOR AND TEMPERATURE SENSOR

(71) Applicant: SEMITEC Corporation, Tokyo (JP)

(72) Inventor: Takafumi Matsushita, Tokyo (JP)

(73) Assignee: SEMITEC Corporation, Tokyo (JP)

( * ) Notice: Subject to any disclaimer, the term of this patent is extended or adjusted under 35 U.S.C. 154(b) by 0 days.

(21) Appl. No.: 15/760,229

(22) PCT Filed: Sep. 9, 2016

(86) PCT No.: PCT/JP2016/076574
§ 371 (c)(1),
(2) Date: Mar. 15, 2018

(87) PCT Pub. No.: WO2017/047512
PCT Pub. Date: Mar. 23, 2017

(65) Prior Publication Data
US 2019/0049316 A1    Feb. 14, 2019

(30) Foreign Application Priority Data
Sep. 16, 2015    (JP) .................................. 2015-183131

(51) Int. Cl.
*G01K 7/22*    (2006.01)
*H01C 7/04*    (2006.01)
(Continued)

(52) U.S. Cl.
CPC .............. *G01K 7/22* (2013.01); *A61B 5/6852* (2013.01); *H01C 7/02* (2013.01); *H01C 7/021* (2013.01);
(Continued)

(58) Field of Classification Search
CPC . H01C 7/041; H01C 7/04; H01C 7/21; G01K 7/22
See application file for complete search history.

(56) References Cited

U.S. PATENT DOCUMENTS 6,544,458 B1 *  4/2003  Hansma .................... B22C 1/00
                                                264/234
6,989,574 B2 *  1/2006  Parsons .................... G01K 7/16
                                                257/417

(Continued)

FOREIGN PATENT DOCUMENTS

CN    101770842    7/2010
JP    H04-006804    1/1992
(Continued)

OTHER PUBLICATIONS

JP 20014-116456 (Year: 2014).*
(Continued)

*Primary Examiner* — Kyung S Lee
(74) *Attorney, Agent, or Firm* — JCIPRNET

(57) ABSTRACT

A resistor which is able to have a reduced thickness for an insulating substrate and in which occurrence of cracking is able to be suppressed during production of the insulating substrate, the production of the resistor and mounting of the substrate, and in which the safety of a medical device is increased by forming the insulating substrate using a biocompatible material; and a temperature sensor are provided. This resistor is provided with: an insulating substrate that has a bending strength of 690 MPa or more and a thickness of 10 to 100 μm; a resistive film that is formed on the insulating substrate; at least a pair of electrode layers, that are electrically connected to the resistive film; and a protective film that covers a region where the resistive film is formed, while forming exposure portions so that at least parts of the electrode layers are exposed therein.

20 Claims, 7 Drawing Sheets

(51) Int. Cl.
    *H01C 7/02*     (2006.01)
    *A61B 5/00*     (2006.01)

(52) U.S. Cl.
    CPC ............... *H01C 7/04* (2013.01); *H01C 7/041* (2013.01); *A61B 2562/0271* (2013.01); *A61B 2562/0276* (2013.01); *A61B 2562/125* (2013.01)

(56) References Cited

U.S. PATENT DOCUMENTS

| | | | | |
|---|---|---|---|---|
| 2004/0224459 | A1* | 11/2004 | Nishikawa | C30B 23/02 438/202 |
| 2010/0104495 | A1* | 4/2010 | Kawabata | C30B 7/10 423/409 |
| 2010/0123370 | A1* | 5/2010 | Yamaguchi | H01L 41/1878 310/365 |
| 2014/0193623 | A1* | 7/2014 | Setoyama | B23B 27/14 428/216 |
| 2015/0036723 | A1* | 2/2015 | Fujita | H01C 7/04 374/185 |

FOREIGN PATENT DOCUMENTS

| | | |
|---|---|---|
| JP | 2000277662 | 10/2000 |
| JP | 2004140285 | 5/2004 |
| JP | 2005228782 | 8/2005 |
| JP | 2007066924 | 3/2007 |
| JP | 4871548 | 2/2012 |
| JP | 2013197367 | 9/2013 |
| JP | 2014090049 | 5/2014 |
| JP | 2014116456 | 6/2014 |
| JP | 5663804 | 2/2015 |

OTHER PUBLICATIONS

JP 2013-197367 (Year: 2013).*
JP 2000-277662 (Year: 2000).*
"International Search Report (Form PCT/ISA/210) of PCT/JP2016/076574", dated Nov. 8, 2016, with English translation thereof, pp. 1-4.
"Office Action of China Counterpart Application," with English translation thereof, dated May 24, 2019, p. 1-p. 14.

* cited by examiner

CRYSTALLINE SYSTEM

| SAMPLE No. | MATERIAL | PURITY [%] | CRYSTAL STATE | | BENDING STRENGTH [MPa] | POSSIBILITY OF FABRICATION OF 50μm |
|---|---|---|---|---|---|---|
| 1 | QUARTZ SiO2 | 100 | AMORPHOUS | | 95 | × |
| 2 | SILICON Si | 100 | SINGLE CRYSTAL | | 78 | × |
| 3 | SAPPHIRE AL2O3 | 100 | SINGLE CRYSTAL | UNRELATED TO C-AXIS | 350 | × |
| 4 | SAPPHIRE AL2O3 | 100 | | PERPENDICULAR TO C-AXIS | 690 | ○ |
| 5 | SAPPHIRE AL2O3 | 100 | | PARALLEL TO C-AXIS | 1035 | ○ |

FIG. 4

CERAMIC

| SAMPLE No. | MATERIAL | PURITY [%] | APPEARANCE | SINTERED PARTICLE DIAMETER [μm] | BENDING STRENGTH [MPa] | POSSIBILITY OF FABRICATION OF 50μm |
|---|---|---|---|---|---|---|
| 1 | ALUMINA AL2O3 | 99.90 | DENSENESS (TRANSPARENT) | 30 | 300 | × |
| 2 | ALUMINA AL2O3 | 99.90 | DENSENESS | 15 | 400 | × |
| 3 | ALUMINA AL2O3 | 99.90 | DENSENESS | 5 | 660 | × |
| 4 | SILICON NITRIDE Si3N4 | 99.90 | DENSENESS | 2 | 900 | ○ |
| 5 | ZIRCONIA ZrO2 | 3%Y | DENSENESS | 0.5 | 1200 | ○ |
| 6 | SIALON Si3N4·Al2O3 | — | DENSENESS | — | 880 | ○ |

FIG. 5

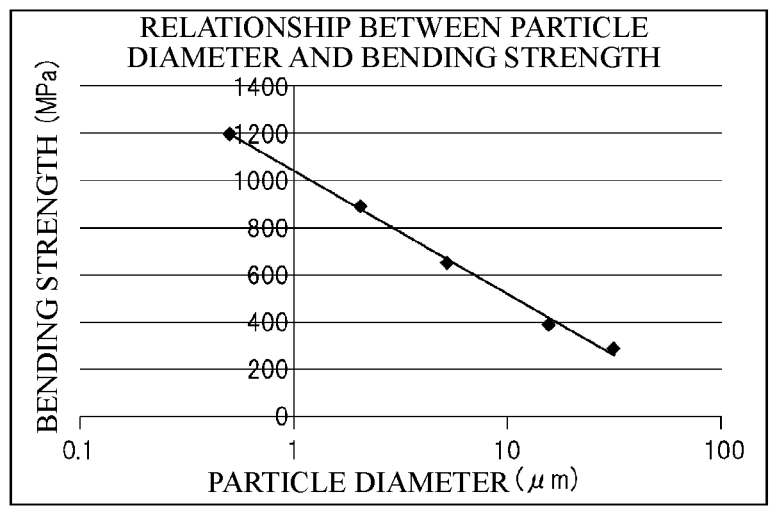

FIG. 6

RESISTOR AND TEMPERATURE SENSOR

CROSS-REFERENCE TO RELATED APPLICATION

This application is a 371 application of the international PCT application serial no. PCT/JP2016/076574, filed on Sep. 9, 2016, which claims the priority benefit of Japan application no. 2015-183131, filed on Sep. 16, 2015. The entirety of each of the above-mentioned patent applications is hereby incorporated by reference herein and made a part of this specification.

TECHNICAL FIELD

The present invention relates to a resistor and a temperature sensor of which a thickness can be reduced.

BACKGROUND ART

An electronic component such as a heat-sensitive resistive element is used, as a resistor, for information communication devices such as moving body communication terminals or personal computers, as well as electronic devices such as wearable devices, medical devices, consumer devices, or automobile electrical devices.

Recently, a reduction in a thickness of such electronic devices has been required, and development of electronic components having a small thickness has been under development due to limitation of a thickness dimension of the electronic devices.

For example, Patent Literature 1 describes a thin film thermistor using a ceramic substrate having a thickness dimension of 50 μm to 300 μm in a chip resistor to be mounted on a board. Patent Literature 2 describes a chip resistor having a thickness dimension of 60 μm to 150 μm. On the other hand, Patent Literature 3 mentions a problem that, when a ceramic substrate in which an insulating substrate has a thickness dimension of 30 μm to 100 μm is used, the substrate may break at the time of fabricating a chip component. Therefore, even when a chip resistor having a thickness dimension of 60 μm according to Patent Literature 2 can be formed, there is concern that the substrate may break, a problem such as cracks at the time of mounting of the board occurring, and a product with extremely low reliability being obtained.

Due to this, it is preferable to use an extremely thin substrate having a thickness dimension of 100 μm or less so that the substrate does not break at the time of fabricating a chip component, and to fabricate a chip resistor and a heat-sensitive resistor using an insulating substrate formed of, for example, a ceramic material of which the reliability such as the stability or heat resistance is high.

On the other hand, in a resistor and a heat-sensitive resistor that are used for a wearable device that monitors biological information, a catheter that is a medical device, or the like, it is required for the resistor and the heat-sensitive resistor to be formed of a material for which biocompatibility is taken into consideration regarding a material to be used when there is a high risk of exposure of the resistor and the heat-sensitive resistor inside a living body.

When a part of the heat-sensitive resistor is formed of a biocompatible material, direct contact with a living body is possible, and an effect that accurate temperature detection of the living body is possible can be expected.

CITATION LIST

Patent Literature

Patent Literature 1: Japanese Patent No. 4871548
Patent Literature 2: Japanese Patent No. 5663804
Patent Literature 3: Japanese Unexamined Patent Application Publication No. 4-6804
Patent Literature 4: Japanese Unexamined Patent Application Publication No. 2004-140285

SUMMARY OF INVENTION

Technical Problem

However, an insulating substrate formed of a ceramic material is hard and brittle. When a thickness of an insulating substrate is reduced, there is concern that the insulating substrate may break and a problem that a yield is reduced in a polishing process when the insulating substrate is fabricated and a process of fabricating the resistor. Further, there is concern that a problem such as cracking when the insulating substrate is mounted on a board (a circuit board) may occur.

Therefore, for example, it is technically difficult to fabricate an insulating substrate having a thin form with a thickness dimension of 100 μm or less, and selecting a material for the insulating substrate with which cracking can be suppressed and which has high strength is becoming an important issue.

The present invention has been made in view of the above problems, and an object of the present invention is to provide a resistor and a temperature sensor in which a thickness of an insulating substrate is able to be reduced, and occurrence of cracking is able to be suppressed at the time of fabricating of the resistor, at the time of fabricating the insulating substrate and at the time of mounting the substrate.

Further, another object of the present invention is to improve the safety of a medical device by forming a resistor and a temperature sensor that are used for a wearable device that monitors biological information, a catheter that is a medical device, or the like, using a material taking biocompatibility into account.

Further, another object of the present invention is to provide a temperature sensor capable of coming in direct contact with a living body by forming a part of a resistor using a biocompatible material and of accurate temperature detection of a living body.

Solution to Problem

A resistor described in claim 1 is characterized in that the resistor includes an insulating substrate having a bending strength of 690 MPa or more and a thickness dimension of 10 μm to 100 μm; a resistive film formed on the insulating substrate; at least a pair of electrode layers electrically connected to the resistive film; and a protective film that covers a region in which the resistive film is formed, and has exposed portions formed to expose at least a part of each of the electrode layers.

According to such an invention, a thickness of the insulating substrate can be reduced, and occurrence of cracks can be suppressed. Note that the resistor may include a resistive film irrespective of its characteristics. Examples of the resistor include a resistor only having electrical resistance, and a thermistor having a negative temperature coefficient or a positive temperature coefficient.

The resistor described in claim 2 is the resistor according to claim 1 characterized in that the insulating substrate is formed of a ceramic material.

The resistor described in claim 3 is the resistor according to claim 1 characterized in that the insulating substrate is formed of a single crystal material.

The resistor described in claim 4 is the resistor according to claim 2 characterized in that an average particle diameter after sintering of the ceramic material is 0.1 μm to 4 μm.

The resistor described in claim 5 is the resistor according to claim 2 or 4 characterized in that a void fraction of the ceramic material after sintering is 3% or less.

The resistor described in claim 6 is the resistor according to claim 2, 4, or 5 characterized in that the ceramic material is zirconia, silicon nitride, or alumina, or a mixture including at least one of these materials.

The resistor described in claim 7 is the resistor according to claim 3 characterized in that the single crystal material is sapphire, and a direction of a crystal axis thereof is perpendicular or parallel to a C-axis.

The resistor described in claim 8 is the semiconductor device according to any one of claims 1 to 7 characterized by including a pair of external electrodes connected to the exposed portion of the electrode layer and formed to cover an end portion of the insulating substrate.

A temperature sensor described in claim 9 is characterized in that a temperature sensor includes a flexible wiring board; and a resistor in which an insulating substrate according to any one of claims 1 to 8 mounted on the flexible wiring board is formed of a biocompatible material.

The biocompatible material in the insulating substrate is not limited to a specific material. For example, zirconia, alumina, or a mixture of at least one of these can be suitably used.

Further, a mounting form of the resistor on the flexible wiring board is not particularly limited. For example, it is possible to mount the resistor on a surface of the flexible wiring board or mount the resistor such that it is built into the flexible wiring board.

A temperature sensor described in claim 10 includes: a flexible wiring board; and the resistor according to claim 9 mounted on the flexible wiring board, the insulating substrate being exposed to the outside.

Advantageous Effects of Invention

According to the present invention, it is possible to provide a resistor and a temperature sensor in which a thickness of an insulating substrate is able to be reduced and occurrence of cracking is able to be suppressed.

Further, when the resistor and the temperature sensor are formed of a biocompatible material, safety can be enhanced and accurate temperature detection of a living body can be performed.

BRIEF DESCRIPTION OF DRAWINGS

FIG. 4 is a table illustrating evaluation results of a crystalline material.

FIG. 5 is a table illustrating evaluation results of a ceramic material.

FIG. 6 is a graph illustrating a relationship between an average particle diameter after sintering and a bending strength of the ceramic material.

DESCRIPTION OF EMBODIMENTS

Figure 1:
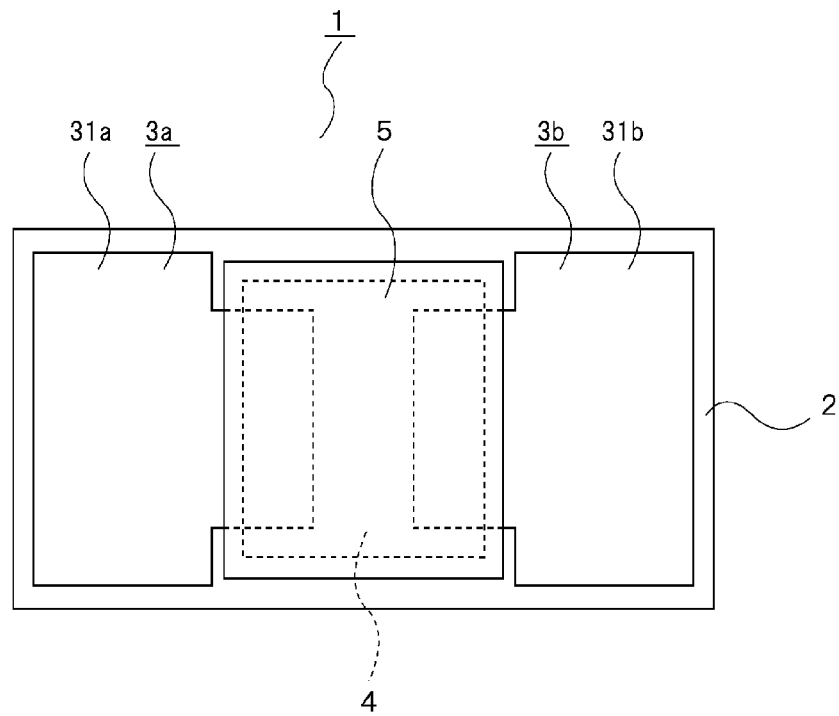
FIG. 1 is a plan view illustrating a resistor according to a first embodiment of the present invention.
Figure 2:
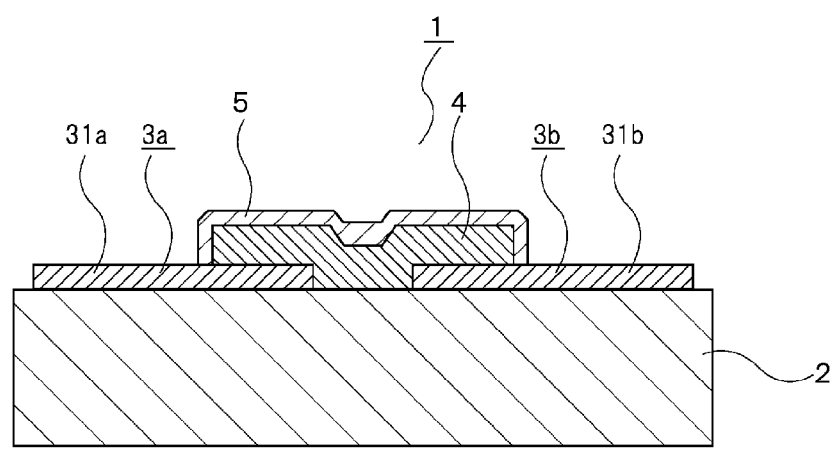
FIG. 2 is a cross-sectional view illustrating the same resistor.
Figure 3:
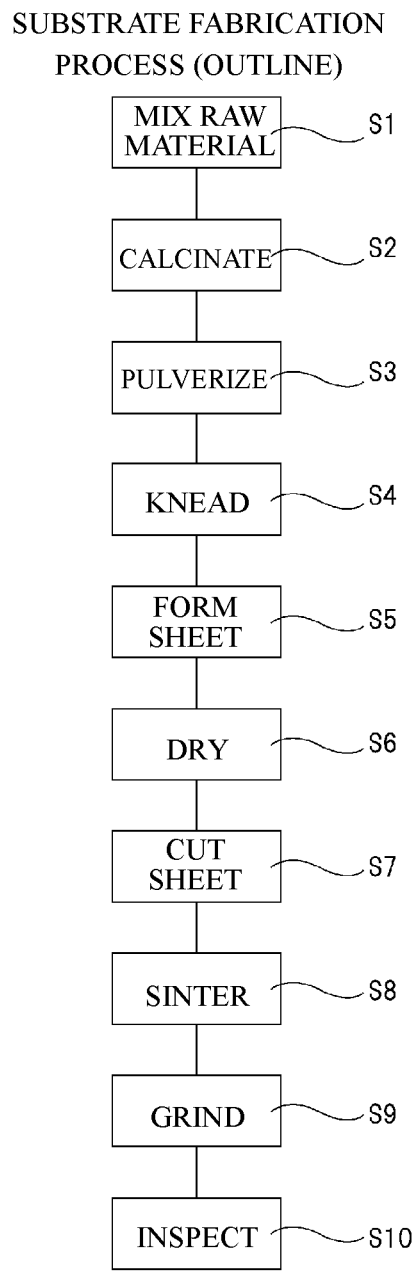
FIG. 3 is a flowchart illustrating an outline of a process of fabricating an insulating substrate.
Figure 7A:
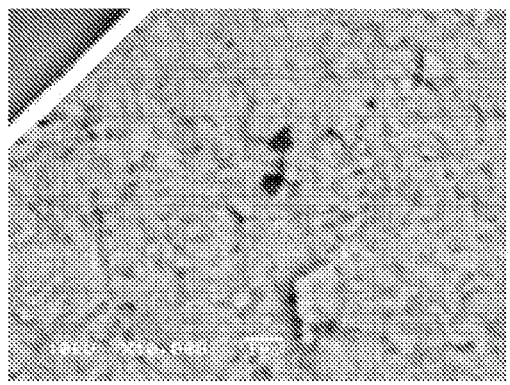
FIG. 7A and FIG. 7B are photographs illustrating observation of a ceramic material after sintering using an electron microscope.
Figure 7B:
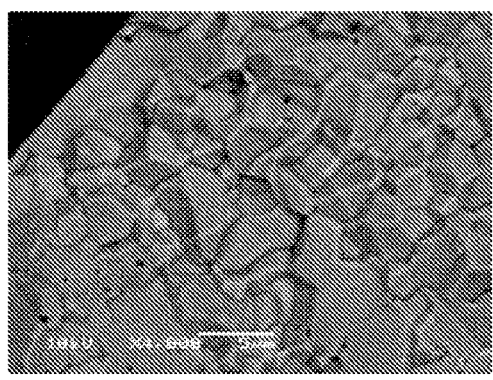

Hereinafter, a resistor according to a first embodiment of the present invention will be described with reference to FIGS. 1 to 7A and 7B. FIGS. 1 and 2 illustrate the resistor, and FIG. 3 schematically illustrates an example of a process of fabricating an insulating substrate. FIGS. 4 to 6 illustrate evaluation results for reducing a thickness of the insulating substrate, and FIG. 7A and FIG. 7B illustrates an example of an electron microscope photograph of the insulating substrate. In the respective drawings, the scale of each member is appropriately changed for the sake of description in order to cause each member to have a recognizable size.

As illustrated in FIGS. 1 and 2, the resistor 1 includes an insulating substrate 2, a pair of electrode layers 3a and 3b, a resistive film 4, and a protective film 5.

In the embodiment, the resistor 1 is a heat-sensitive resistive element and is a thin film thermistor. Note that the resistor may include a resistive film irrespective of its characteristics. Examples of the resistor may include a resistor only having electrical resistance, and a thermistor having a negative temperature coefficient or a positive temperature coefficient.

The resistor 1 is formed in a substantially rectangular parallelepiped shape, and has a lateral dimension of 1.0 mm, a longitudinal dimension of 0.5 mm, and a total thickness dimension of 40 μm. The shape and the size are not particularly limited, and can be appropriately selected depending on a use of the resistor 1.

The insulating substrate 2 has a substantially rectangular shape and is formed using a ceramic material such as insulating zirconia, silicon nitride, alumina, or a mixture of at least one of these materials. This insulating substrate 2 is formed to have a thickness dimension of 50 μm or less, specifically, 10 μm to 50 μm, and preferably 30 μm or less. Further, a bending strength of the insulating substrate 2 is 690 MPa or more, and an average particle diameter of the insulating substrate 2 after the ceramic material is sintered is 0.1 μm to 4 μm.

Further, zirconia, alumina, and composites thereof have been used as dental materials, and are materials for which biocompatibility has been confirmed. Therefore, for example, zirconia, alumina, or a mixture of at least one of these materials can be suitably used as a biocompatible material of the insulating substrate in the resistor 1 that is used for a wearable device that monitors biological information, a catheter that is a medical device, or the like.

Note that, as will be described in detail below, the present inventors conducted various investigations and selection work in the development process, focused on a bending strength of the insulting substrate 2, and found that as a condition for fabricating the insulating substrate 2 so that a thickness dimension thereof was 50 μm or less, a value of a bending strength had to be 690 MPa or more.

The pair of electrode layers 3a and 3b are formed on the insulating substrate 2, are portions to which the resistive film 4 is electrically connected, and are arranged to face each other with a predetermined interval therebetween. Specifically, the pair of electrode layers 3a and 3b are formed by forming a thin metal film using a sputtering method, and as a metal material thereof, a noble metal such as platinum (Pt), gold (Au), silver (Ag), palladium (Pd), or ruthenium (Ru), or an alloy thereof such as an Ag—Pd alloy is used.

These noble metals and alloys thereof are used as dental materials and the biocompatibility thereof has been confirmed.

Note that in the embodiment, the electrode layers 3a and 3b are formed under the resistive film 4, but may be formed on or in the resistive film 4.

The resistive film 4 is a thermosensitive thin film and is a thin film thermistor formed of an oxide semiconductor having a negative temperature coefficient. The resistive film 4 is formed on the electrode layers 3a and 3b using a sputtering method to straddle the electrode layers 3a and 3b, and is electrically connected to the electrode layers 3a and 3b.

The resistive film 4 is formed of two or more elements selected from transition metal elements such as manganese (Mn), nickel (Ni), cobalt (Co), and iron (Fe), and is formed of a thermistor material containing a composite metal oxide having a spinel structure as a main component. Further, subcomponents may be included, for example, for improvement of characteristics. A composition and contents of the main component and subcomponents can be appropriately determined according to desired characteristics.

When a resistor is used for a wearable device that monitors biological information, a catheter that is a medical device, or the like, it is preferable to use noble metals of which biocompatibility has been confirmed as the material of the resistive film.

In this case, a noble metal such as platinum (Pt), gold (Au), silver (Ag), palladium (Pd), ruthenium (Ru), or an alloy thereof such as an Ag—Pd alloy may be used for a metal material for the resistive film. In the case of an oxide, a ruthenium oxide that is an oxide of a noble metal, or the like can be used.

When the resistive film is a thin heat-sensitive film, platinum (Pt) as a noble metal, silicon carbide (SiC) as a ceramic semiconductor, silicon nitride (SiN), a mixture thereof, or the like can be used as a material of the resistive film.

The protective film 5 covers a region in which the resistive film 4 is formed, and has exposed portions 31a and 31b formed to expose at least a part of each of the electrode layers 3a and 3b to cover the electrode layers 3a and 3b. The protective film 5 can be formed by forming silicon dioxide, silicon nitride, or the like using a sputtering method, or by forming lead glass, borosilicate glass, lead borosilicate glass, or the like using a printing method.

When the resistor is used for a wearable device that monitors biological information, a catheter that is a medical device, or the like, it is preferable to use a biocompatible glass as the material of the protective film. An example of the biocompatible glass includes calcium phosphate glass.

Further, it is preferable to use glass that does not contain harmful lead (Pb) or cadmium (Cd).

Next, an example of a process of fabricating the insulating substrate 2 will be described with reference to FIG. 3. FIG. 3 is a flowchart illustrating an outline of a fabricating process.

As illustrated in FIG. 3, the process of fabricating the insulating substrate 2 includes a process of combining and mixing ceramic powders in certain proportions (raw material mixing process (S1)), a process of oxidizing a raw material and sintering the raw material at a lower temperature than in main calcining (sintering process (S2)), a process of pulverizing the raw material to a predetermined particle diameter (pulverizing process (S3)), a process of mixing the pulverized raw material and a small amount of liquid in a slurry state (kneading process (S4)), a process of forming a green sheet (sheet forming process (S5)), a process of drying the green sheet (drying process (S6)), a process of cutting the green sheet to a working size (sheet cutting process (S7)), a process of heating the cut ceramic material (sintering process (S8)), a process of grinding the sintered ceramic material to form a substrate having a predetermined thickness dimension (grinding process (S9)), and a process of inspecting, for example, the dimensions or whether chipping is present (inspection process (S10)).

Here, an average particle diameter of the ceramic material after the sintering process (S8) is 0.1 μm to 4 μm, and a thickness dimension of the substrate after polishing in the grinding process (S9) is 10 μM to 50 μm.

Note that each of the above process is not particularly limited, and the insulating substrate 2 may be formed to have an average particle diameter after sintering of 0.1 μm to 4 μm and a thickness dimension of 10 μm to 50 μm.

Subsequently, in FIGS. 4 to 6, evaluation results when the insulating substrate 2 of which a thickness can be reduced and in which the occurrence of cracks can be suppressed was fabricated will be described. FIG. 4 is a table illustrating evaluation results of crystalline materials, and FIG. 5 is a table illustrating evaluation results of ceramic materials. FIG. 6 is a graph illustrating a relationship between a particle diameter and bending strength in the ceramic material.

Example 1

FIG. 4 illustrates evaluation results as to whether or not an insulating substrate having a thickness dimension of 50 μm can be manufactured with respect to crystalline materials. Among a large number of samples, the main results of various observations and measurements are illustrated in Sample No. 1. to No. 5.

As illustrated in FIG. 4, evaluation results that an insulating substrate having a thickness dimension of 50 μm could be fabricated were obtained for No. 4 and No. 5 samples. No. 4 is sapphire, and has a crystal state of a single crystal and a direction of a crystal axis perpendicular to a C-axis. Further, a bending strength of this sapphire was 690 MPa. No. 5 is also sapphire, and has a crystal state of a single crystal, and a direction of a crystal axis parallel to the C-axis. Further, a bending strength of this sapphire is 1035 MPa.

From such evaluation results, it was confirmed that an insulating substrate having a thickness dimension of 50 μm or less can be manufactured as long as the bending strength has a value of 690 MPa or more. Specifically, the present inventor has succeeded in fabrication of a 30 μm insulating substrate using sapphire having a bending strength of 690 MPa, and fabrication of a resistor using this substrate.

Further, since components of the sapphire are the same as those of alumina, sapphire is a material of which biocompatibility has been confirmed.

Example 2

FIG. 5 illustrates evaluation results as to whether or not an insulating substrate having a thickness dimension of 50 μm can be manufactured with respect to ceramic materials. Six samples which are No. 1 to No. 6 are illustrated.

As illustrated in FIG. 5, evaluation results that an insulating substrate having a thickness dimension of 50 μm can be fabricated were obtained for samples of No. 4, No. 5, and No. 6. No. 4 is silicon nitride, and has an average particle diameter after sintering of 2 μm and a bending strength of 900 MPa. No. 5 is zirconia, and has an average particle diameter after sintering of 0.5 μm, and a bending strength of 1200 MPa. No. 6 is a sialon and has bending strength of 880 MPa.

From such evaluation results, it was confirmed that an insulating substrate having a thickness dimension of 50 μm or less could be fabricated as long as the bending strength has a value of 690 MPa or more on the basis of the evaluation result of Example 1.

In this case, as illustrated in FIG. 6, it can be seen that the bending strength and the average particle diameter after sintering have a correlation. That is, the bending strength increases as the average particle diameter after sintering decreases.

FIG. 6 is a graph illustrating a relationship between the average particle diameter after sintering and the bending strength, on the basis of the evaluation result of FIG. 5. A horizontal axis indicates particle diameter (μm), and a vertical axis indicates the bending strength (MPa). Since the bending strength increases as the particle diameter decreases, and, as described above, the particle diameter at which the bending strength becomes 690 MPa or more is 4 μm or less from the evaluation result of FIG. 5 and the graph of FIG. 6, and a particle diameter at which sintering is possible has a lower limit of 0.1 μm, a specific range of 0.1 μm to 4 μm can be obtained.

The bending strength of general alumina is 400 MPa or less. A limit for the dimension of a thickness that can be processed in this case is about 100 μm. Further, in alumina having a bending strength of 660 MPa, the limit is 70 μm. The present inventors have succeeded in fabrication of a 30 μm insulating substrate using zirconia having a bending strength of 1200 MPa and fabrication of a resistor using this substrate.

FIG. 7A and FIG. 7B illustrates observation of the ceramic materials after sintering using an electron microscope. FIG. 7A is a photograph of the zirconia of No. 5 and FIG. 7B is a photograph of the alumina of No. 3. It can be seen that the zirconia of No. 5 has a small void (a black part on the photograph) in contrast to the alumina of No. 3. Therefore, it is necessary that there are few defects and it is preferable for a void fraction to be 3% or less in order to increase the bending strength.

As described above, according to the embodiment, it is possible to provide the resistor 1 in which the thickness of the insulating substrate 2 can be reduced and occurrence of cracks can be suppressed.

In a case where the insulating substrate 2 is fabricated in a thin shape having a thickness dimension of 100 μm or less, there is concern that the insulating substrate 2 may be easily bent when the bending strength is low, and a problem arise in that the resistance of the resistive film 4 changes when the insulating substrate 2 is deformed. Therefore, it is preferable for the insulating substrate 2 that is used for the resistor 1 to have a high bending strength.

Next, a resistor according to a second embodiment of the present invention will be described with reference to FIGS. 8A and 8B and FIGS. 9A and 9B. Note that in each of the following embodiments, parts that are the same as or correspond to those in the first embodiment are denoted with the same reference numerals, and repeated descriptions thereof will be omitted.

Figure 8A:
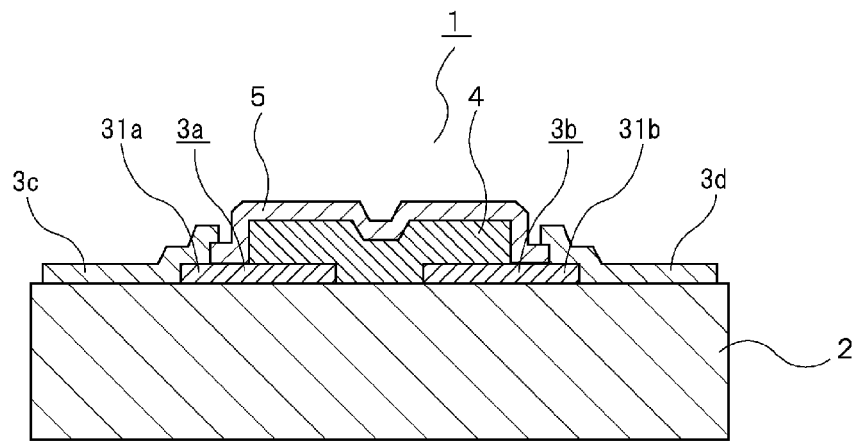
FIG. 8A and FIG. 8B are respectively a cross-sectional view and a plan view illustrating a resistor according to a second embodiment of the present invention.
Figure 8B:
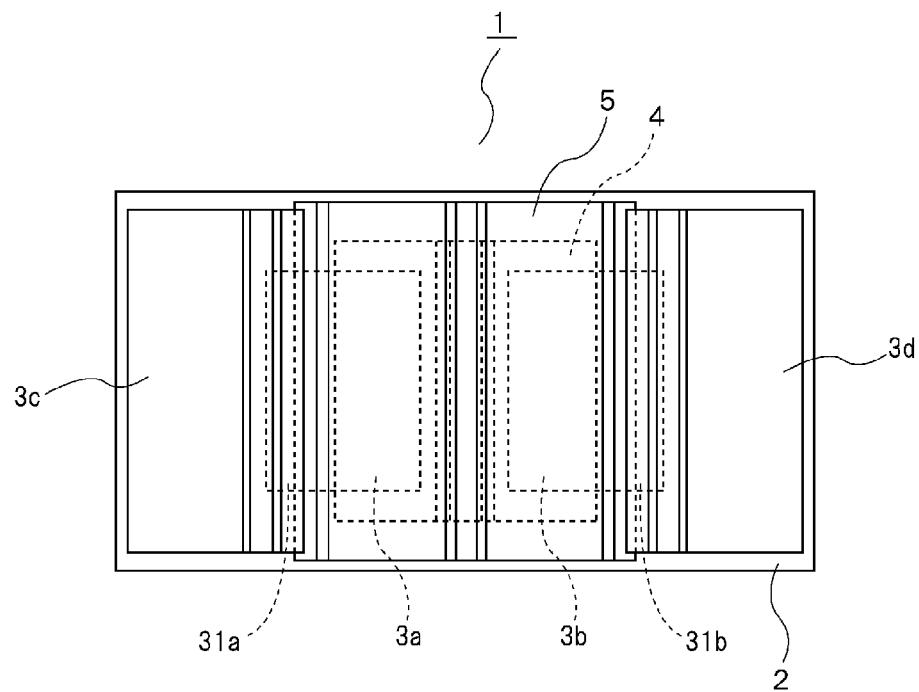

As illustrated in FIG. 8A and FIG. 8B, the resistor 1 of the second embodiment has basically the same configuration as the resistor 1 of the first embodiment. In the second embodiment, the resistor 1 includes a pair of external electrodes 3c and 3d formed on an insulating substrate 2 and connected to exposed portions 31a and 31b of electrode layers 3a and 3b. The external electrodes 3c and 3d are formed of copper (Cu). Further, a thickness dimension is 6 μm to 10 μm.

When the resistor 1 is built into and mounted on a circuit board, it is preferable for a thickness dimension of the external electrodes 3c and 3d (not illustrated) to exceed a thickness dimension of a protective film 5. The external electrodes 31a and 31b function as stopper layers for protecting, for example, an internal electrode or a second internal electrode from impact from a laser beam when a via is formed using laser beam etching in a case in which the resistor 1 is mounted, and good connectivity to a wiring layer of the circuit board can be obtained.

Further, using a method of building the resistor 1 into the circuit board, the resistor 1 may be embedded in an insulator of the circuit board, and then, vias may be formed in an insulating layer covering the chip resistor 1 through radiation of a laser beam such that the external electrodes 3c and 3d are exposed and connected to external wirings, and it is preferable for the external electrodes 3c and 3d to be as large as possible in order to form the vias.

Figure 9A:
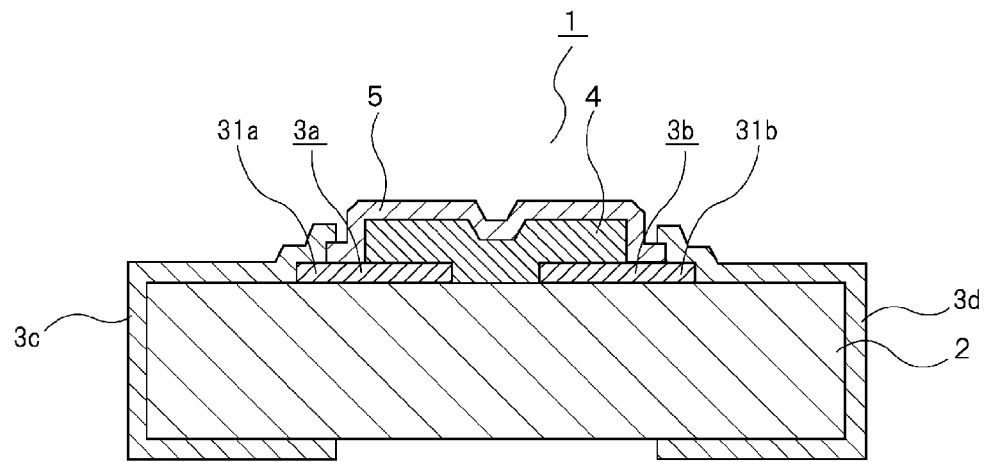
FIG. 9A and FIG. 9B are respectively a cross-sectional view and a plan view illustrating a resistor according to the second embodiment.
Figure 9B:
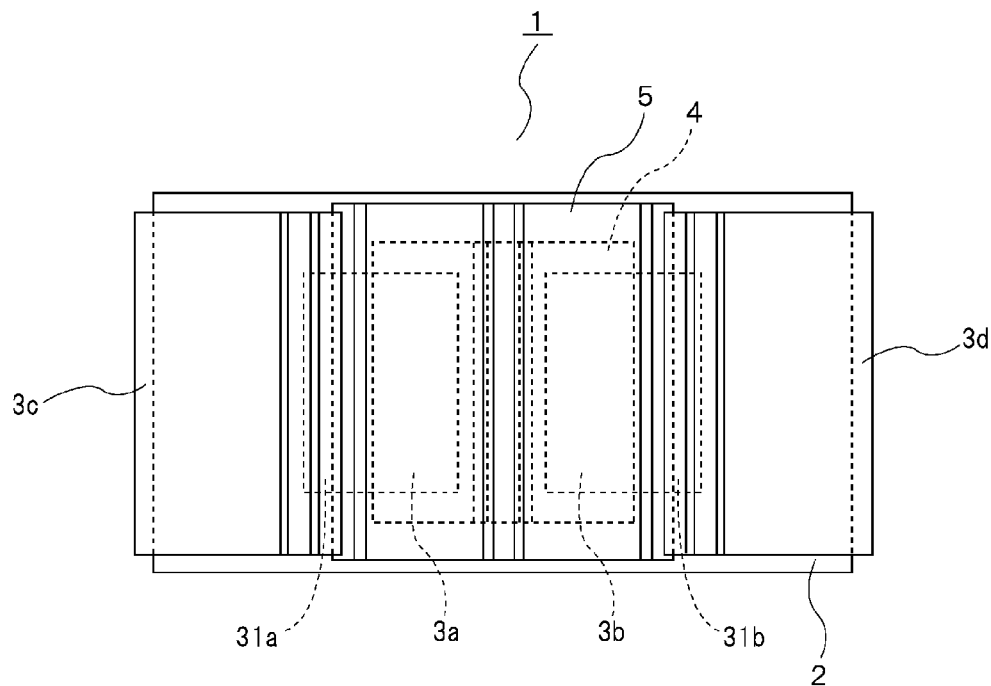

Further, as illustrated in FIG. 9A and FIG. 9B, a pair of external electrodes 3c and 3d may be formed to be connected to the exposed portions 31a and 31b of the electrode layers 3a and 3b and to cover an end portion of the insulating substrate 2. The external electrodes 3c and 3d are formed of a copper (Cu) material and have a substantially U-shaped cross section, and a thickness dimension thereof is 6 μm to 10 μm. According to such a configuration, for example, it is easy for the resistor 1 to be mounted in a face-down or face-up form.

Note that when the external electrodes 3c and 3d are formed as thin films, the external electrodes 3c and 3d may be formed in a multilayer structure in which titanium (Ti), platinum (Pt), and gold (Au) are laminated.

When the resistor 1 is used for a wearable device that monitors biological information, a catheter that is a medical device, or the like, it is preferable for electrode materials thereof to be formed of a material of which biocompatibility has been confirmed.

Further, this electrode configuration can be formed to be extremely thin. A thickness dimension of titanium (Ti) is 0.02 μm, a thickness dimension of platinum (Pt) is 0.2 μm, and a thickness dimension of gold (Au) is 0.2 μm. The electrode configuration can be formed as a very thin electrode having a total thickness of multiple layers of 0.5 μm or less. A 1 μm or less electrode configuration like this is the best configuration when the thin substrate of the present invention is used.

Further, although this electrode configuration is unsuitable for continuous use at a temperature exceeding 100° C., the electrode configuration is sufficient for use in a wearable device that monitors biological information, a catheter that is a medical device, or the like.

It was confirmed that no problems occur in a solder connection portion even in a high temperature test at 100° C. for 1000 hours when the electrodes as described above were mounted on a resistor with a lead-free solder containing no harmful lead (Pb).

In a third embodiment to be described below, an effect of a configuration in which the resistor 1 is mounted on the circuit board 10 by being built into the circuit board 10 according to the second embodiment described above being facilitated, can be expected.

Figure 10:
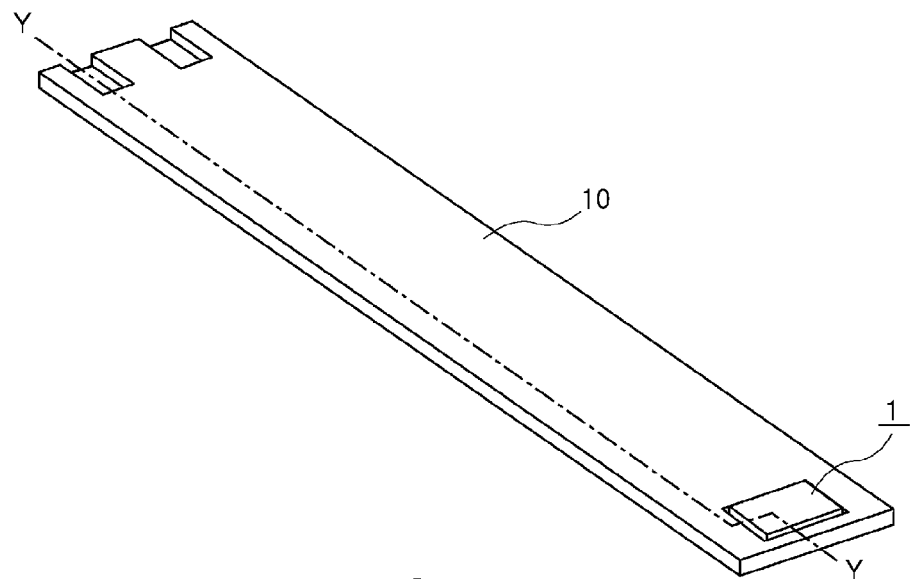
FIG. 10 is a perspective view illustrating a temperature sensor according to a third embodiment of the present invention.
Figure 11:
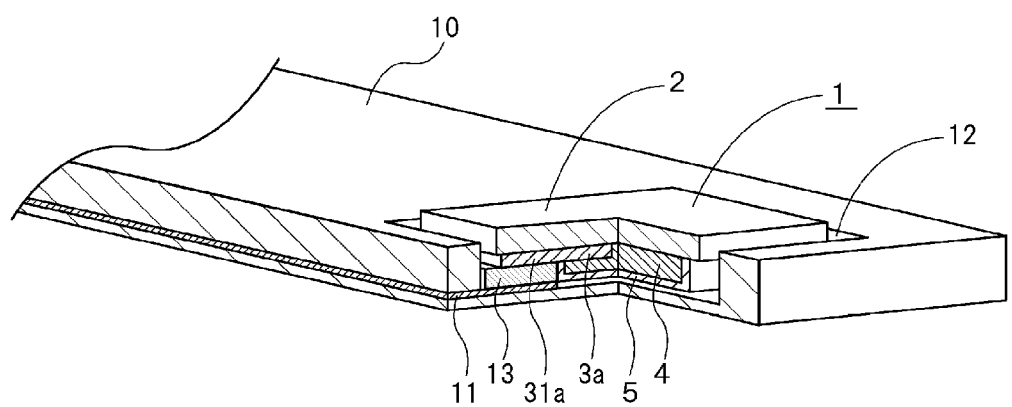
FIG. 11 is a cross-sectional view taken along a line Y-Y in FIG. 10.

Subsequently, a temperature sensor according to the third embodiment of the present invention will be described with reference to FIGS. 10 and 11. FIG. 10 illustrates a perspective view of the temperature sensor, and FIG. 11 schematically illustrates a part of a cross section taken along a line Y-Y in FIG. 10.

In this embodiment, a temperature sensor in which the resistor 1 is mounted on the circuit board 10 is illustrated. The circuit board 10 is a flexible wiring board (FPC) having flexibility formed in a substantially elongated rectangular shape. For the circuit board 10, a resin formed of a polymer material such as a polyimide, polyethylene, a liquid crystal polymer, a fluorine resin, a silicone, polyester, polycarbonate, or polyphenylene sulfide (PPS) can be used.

For a wearable device that monitors biological information, a catheter that is a medical device, or the like, it is preferable for a biocompatible resin material to be used for a material of the circuit board 10. Resin materials such as a polyimide, a polyamide, a polyester, a silicone resin, and a fluorine resin of which biocompatibility has been confirmed can be used.

A wiring pattern 11 of a conductor is formed within the thickness of the circuit board 10. Further, a cavity 12 in which the resistor 1 is embedded is formed on one end side of the circuit board 10, and the resistor 1 is mounted in a face-down form in this cavity 12. Further, the exposed portions 31a and 31b of the electrode layers 3a and 3b in the resistor 1 and the wiring pattern 11 of the circuit board 10 are electrically connected by a connection material 13 such as solder.

Further, a thickness dimension of the circuit board 10 is 60 μm to 80 μm and, preferably, 70 μm, a thickness dimension of the insulating substrate 2 is 20 μm to 50 μm and, preferably, 30 μm, a total thickness of the resistor 1 is 30 μm to 60 μm and, preferably, 40 μm, and a total thickness in a state in which the resistor 1 is mounted on the circuit board 10 is 80 μm to 120 μm and, preferably, 100 μm.

When the cavity 12 is sealed with a biocompatible silicone resin or the like, only the insulating substrate 2 of the resistor 1 is exposed. In such a state, when the insulating substrate 2 is formed of alumina, zirconia, sapphire, or the like of which biocompatibility has been confirmed, the insulating substrate 2 can come in direct contact with a living body, and accurate temperature detection can be performed.

Meanwhile, a wearable device that monitors general biological information, a medical temperature sensor such as a catheter that is a medical device, or the like does not take biocompatibility into account. Therefore, the entire temperature sensor including the insulating substrate 2 is covered with, for example, a biocompatible silicone resin so that the temperature sensor itself is not exposed to the outside. Therefore, since the (heat-sensitive) resistor 1 does not come in direct contact with the living body, a problem arises in that accurate temperature detection cannot be performed.

As described above, according to the embodiment, it is possible to provide a thinned temperature sensor. Further, when the resistor 1 and the temperature sensor are formed of a biocompatible material, safety can be enhanced and accurate temperature detection of a living body can be performed.

Further, the resistor 1 of the present invention can be applied to an infrared temperature sensor. In this case, the resistive film 4 is a thermosensitive thin film, and an infrared detection thermosensitive element and a temperature compensation thermosensitive element are disposed, as the resistor 1, with a predetermined interval therebetween on one surface of a flexible wiring board.

Note that the present invention is not limited to the configurations of each of the above embodiments, and various modifications can be performed without departing from the gist of the invention. Further, the above-described embodiment is presented as an example, and it is not intended to limit the scope of the invention. These novel embodiments can be implemented in various other forms, and various omissions, substitutions, and changes can be performed. These embodiments or modifications thereof are included in the scope or gist of the invention and are included in the invention described in claims and an equivalent scope thereof.

The invention claimed is:

1. A heat-sensitive resistor comprising:
    an insulating substrate having bending strength of 690 MPa or more and a thickness dimension of 10 μm to 100 μm;
    a thermosensitive thin film formed on the insulating substrate;
    at least a pair of electrode layers electrically connected to the thermosensitive thin film; and
    a protective film that covers a region in which the thermosensitive thin film is formed, and having exposed portions formed to expose at least a part of the pair of electrode layers.

2. The heat-sensitive resistor according to claim 1, wherein the insulating substrate is formed of a ceramic material.

3. The heat-sensitive resistor according to claim 1, wherein the insulating substrate is formed of a single crystal material.

4. The heat-sensitive resistor according to claim 2, wherein an average particle diameter after sintering of the ceramic material is 0.1 μm to 4 μm.

5. The heat-sensitive resistor according to claim 2, wherein a void fraction of the ceramic material after sintering is 3% or less.

6. The heat-sensitive resistor according to claim 2, wherein the ceramic material is zirconia, silicon nitride, alumina, or a mixture of at least one of these materials.

7. The heat-sensitive resistor according to claim 3, wherein the single crystal material is sapphire, and a direction of a crystal axis of the single crystal material is perpendicular or parallel to a C-axis.

8. The heat-sensitive resistor according to claim 1, comprising:
    a pair of external electrodes connected to the exposed portion of the electrode layer and formed to cover an end portion of the insulating substrate.

9. A temperature sensor comprising:
    a flexible wiring board; and
    the heat-sensitive resistor according to claim 1 mounted on the flexible wiring board, in which the insulating substrate is formed of a biocompatible material.

10. A temperature sensor comprising:
a flexible wiring board; and
the heat-sensitive resistor according to claim 9 mounted on the flexible wiring board, wherein the insulating substrate is being exposed to the outside.

11. The heat-sensitive resistor according to claim 4, wherein a void fraction of the ceramic material after sintering is 3% or less.

12. The heat-sensitive resistor according to claim 4, wherein the ceramic material is zirconia, silicon nitride, alumina, or a mixture of at least one of these materials.

13. The heat-sensitive resistor according to claim 5, wherein the ceramic material is zirconia, silicon nitride, alumina, or a mixture of at least one of these materials.

14. The heat-sensitive resistor according to claim 2, comprising:
a pair of external electrodes connected to the exposed portion of the electrode layer and formed to cover an end portion of the insulating substrate.

15. The heat-sensitive resistor according to claim 3, comprising:
a pair of external electrodes connected to the exposed portion of the electrode layer and formed to cover an end portion of the insulating substrate.

16. The heat-sensitive resistor according to claim 4, comprising:
a pair of external electrodes connected to the exposed portion of the electrode layer and formed to cover an end portion of the insulating substrate.

17. The heat-sensitive resistor according to claim 5, comprising:
a pair of external electrodes connected to the exposed portion of the electrode layer and formed to cover an end portion of the insulating substrate.

18. The heat-sensitive resistor according to claim 6, comprising:
a pair of external electrodes connected to the exposed portion of the electrode layer and formed to cover an end portion of the insulating substrate.

19. The heat-sensitive resistor according to claim 7, comprising:
a pair of external electrodes connected to the exposed portion of the electrode layer and formed to cover an end portion of the insulating substrate.

20. A temperature sensor comprising:
a flexible wiring board; and
the heat-sensitive resistor according to claim 2 mounted on the flexible wiring board, in which the insulating substrate is formed of a biocompatible material.

* * * * *